United States Patent
Vargas Diaz et al.

(10) Patent No.: US 11,786,376 B2
(45) Date of Patent: Oct. 17, 2023

(54) PARTICULATE BIOMATERIAL CONTAINING PARTICLES HAVING GEODESIC FORMS, METHOD OF MAKING THE SAME AND USING FOR FILLING OR BONE TISSUE SUBSTITUTION

(71) Applicant: Pontificia Universidad Catolica de Chile, Santiago (CL)

(72) Inventors: Alex Patricio Vargas Diaz, Providencia Santiago (CL); Jorge Andres Ramos Grez, Lo Barnechea Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 779 days.

(21) Appl. No.: 16/621,207

(22) PCT Filed: Aug. 16, 2018

(86) PCT No.: PCT/CL2018/050066
§ 371 (c)(1),
(2) Date: Dec. 10, 2019

(87) PCT Pub. No.: WO2019/041054
PCT Pub. Date: Mar. 7, 2019

(65) Prior Publication Data
US 2020/0205983 A1    Jul. 2, 2020

(30) Foreign Application Priority Data
Aug. 29, 2017  (CL) .................................. 2194-2017

(51) Int. Cl.
*A61F 2/28* (2006.01)
*A61L 27/12* (2006.01)
(Continued)

(52) U.S. Cl.
CPC ................ *A61F 2/28* (2013.01); *A61L 27/12* (2013.01); *A61L 27/365* (2013.01); *A61L 27/56* (2013.01);
(Continued)

(58) Field of Classification Search
CPC ....................................................... A61F 2/28
See application file for complete search history.

(56) References Cited

U.S. PATENT DOCUMENTS

| 2009/0220475 | A1 | 9/2009 | Bohner et al. |
| 2016/0184103 | A1* | 6/2016 | Fonte ...................... A61L 27/56 623/23.5 |
| 2016/0331538 | A1 | 11/2016 | Vogt |

FOREIGN PATENT DOCUMENTS

| WO | 2007084725 A2 | 7/2007 |
| WO | 2009048314 A1 | 4/2009 |

OTHER PUBLICATIONS

Kruyt, Toward Injectable Cell Based Tissue-Engineered Bone: The Effect of Different Calcium Phosphate Microparticles and Pre-Culturing, Tissue Engineering, 12(2), 309-317. (Year: 2006).*

(Continued)

*Primary Examiner* — Carlos A Azpuru
(74) *Attorney, Agent, or Firm* — LUCAS & MERCANTI, LLP (57) ABSTRACT

Particulate biomaterial containing particles having geodesic shapes for filling or replacement of bone tissue, and a method of making the particulate biomaterial containing particles having geodesic shapes for filling or replacement of bone tissue, made by rapid prototyping technique (RP), wherein said particles have non-prismatic, semi-spherical geodesic forms.

12 Claims, 6 Drawing Sheets

(51) Int. Cl.
*A61L 27/36* (2006.01)
*A61L 27/56* (2006.01)
*A61L 27/58* (2006.01)
*A61L 27/00* (2006.01)

(52) U.S. Cl.
CPC ......... *A61L 27/58* (2013.01); *A61F 2240/002* (2013.01); *A61L 27/00* (2013.01)

(56) References Cited

OTHER PUBLICATIONS

M.C. Kruyt, et al; Towards injectable cell-based tissue-engineered bone: the effect of different calcium phosphate microparticles and pre-culturing; Tissue Engineering; vol. 12; No. 2; 2006; pp. 309-317.

E.M. Fischer, et al; Bone formation by mesenchymal progenitor cells cultured on dense and microporous hydroxyapatite particles; Tissue Engineering; vol. 9; No. 6; 2003; pp. 1179-1188.

R. Lowmunkong, et al; Fabrication of freeform bone-filling calcium phosphate ceramics by gypsum 3D printing method; Journal of Biomedical Materials Research Part B: Applied Biomater.; vol. 90; No. 2; 2009; pp. 531-539.

M.A. Goldberg, et al; Gypsum transformation to calcium phosphates; Chemical Technology; Doklady Chemistry; vol. 444; Part 1; 2012; pp. 124-127.

M. Bohner, et al; Synthesis of spherical calcium phosphate particles for dental and orthopedic applications Biomatter; vol. 3; No. 2; 2013; 16 pages.

S.J. Lee, et al; Substrate curvature restricts spreading and induces differentiation of human mesenchymal stem cells; Biotechnology Journal; vol. 12; No. 9; 2017; 10 pages.

S. Choi, et al; Development and evaluation of tetrapod-shaped granular artificial bones; Acta Biomaterialia; vol. 8 2012; pp. 2340-2347.

International Search Report dated Oct. 17, 2018 for PCT/CL2018/050066 and English translation.

* cited by examiner

PARTICULATE BIOMATERIAL CONTAINING PARTICLES HAVING GEODESIC FORMS, METHOD OF MAKING THE SAME AND USING FOR FILLING OR BONE TISSUE SUBSTITUTION

CROSS REFERENCE TO RELATED APPLICATION

This Application is a 371 of PCT/CL2018/050066 filed on Aug. 16, 2018, which, in turn, claimed the priority of Chilean Patent Application No. 2194-2017 filed on Aug. 29, 2017, both applications are incorporated herein by reference.

FIELD OF THE INVENTION

The present invention relates to a filler particle consisting of a biomaterial to be applied in a synthetic graft of bone tissue or other connective tissue, made by 3D Rapid Prototyping (RP) technique, it has a non-prismatic complex geometry, preferably geodesic semi-spherical.

Complex geometry is responsible for the analysis of topological spaces that have some additional structure: they are locally similar to a real or complex space. Concrete examples of this are the so-called Riemann Surfaces which are "locally flat", i.e., similar to a two-dimensional real space (or a one-dimensional complex space). We can envision a sphere (which globally is not flat but, if we imagine ourselves standing over it and watching around, we can perceive it as flat), a tire or doughnut (called complex torus), or the result of attaching 2 or 3 tires, etc. Among these spaces, called Complex Varieties, we are particularly interested in those having symmetries, that is, those that are aesthetically more interesting.

Some of these varieties have a representation as a solution of polynomial equations systems in some large space, called Abelian varieties, which have been extensively studied by Riemann, Abel and Poincare. Recently their study has been revitalized because they have been found to have applications in the Physics field where they are described as Prym-Tyurin varieties: varieties that live inside another and have certain good properties in this context.

Non-prismatic geometry is related to antiprisms where joining edges and faces are not perpendicular to the base faces. This applies if the joining faces are rectangular. If the joining edges and faces are not perpendicular to the base faces, it is called oblique prism.

Semi-spherical geodesic is related to a geodesic dome that is part of a geodesic sphere, a polyhedron generated from an icosahedron or a dodecahedron, although they can be generated from any of the platonic solids. The faces of a geodesic dome can be triangles, hexagons or any other polygon. The vertices must all coincide with the surface of a sphere or an ellipsoid (if the vertices are not on the surface, the dome is no longer geodesic). The number of times that the edges of the icosahedron or dodecahedron are subdivided into smaller triangles is called the frequency of the sphere or geodesic dome. Thus, usually we have domes from frequency 1 (V1) up to the sixth (V6). The higher the frequency, the more the dome is similar to a sphere, since it contains a greater number of vertices.

State of the Art

There is now a great need in the prior art, in the field of orthopedic surgery and dental applications, for biocompatible and bioresorbable implant materials that can be used as a bone substitute in the field of orthopedic surgery and dental applications. Involving cases such as loss of bone tissue due to periodontal disease, increased ridge, bone defects or bone cavities caused by trauma or surgery, and spinal fusion. After implantation, the bone substitute is reabsorbed and replaced by the formation of a new bone, which takes time.

Currently, autogenous bone is being used quite frequently for bone repair or bone tissue replacement in orthopedic surgery. The autogenous bone has good biocompatibility, is not subject to immunological rejection and induces bone growth. However, it requires an additional surgery and, therefore, increases the patient burden while delaying the recovery. On the other hand, both homogeneous bone from other human sources and heterogeneous bone from animal sources always suffer from the disadvantages of adverse immunological reactions. This will result in an inflammatory reaction and rejection after implantation.

The quality of the invention patents documents closets to the present application has been determined.

1. Porous coating for a medical implant, in which the porous coating comprises a porous shape memory material as detailed below;

US 20160184103 A1. Porous coating for orthopedic implant utilizing porous, shape memory materials. The abstract discloses a porous coating for a medical implant, wherein the porous coating comprises a porous, shape memory material.

The invention provides a new porous dynamic implant consisting of a shape memory material, e.g., Nitinol, near beta or fully beta titanium alloys, shape memory polymers (thermoplastic block copolymers) and biodegradable shape memory polymer systems, all of which can be processed to have superelasticity and/or shape recovery. These dynamic porous implants comprise a 3D porous structure, such as, for example, honeycomb. The pores can be infiltrated with a mixture of hydroxyapatite, tricalcium phosphate and other bone promoting agents known in the art. This invention finds utility as dynamic porous implant where fixation and osseointegration are essential, e.g., fillers for bones hollow portions, cement spacers, femoral and tibial cone augmentations, abutments, cages and other bone augmentation devices including bone wedges, such as Evans and Cotton Wedges.

In the present invention, the honeycomb structure can be 3D, such as a dodecahedron structure, similar to nano buckyballs geometry and can be superelastic and/or have SME (shape memory effect via temperature change). It may also be made up of a repeating pattern of diamonds, hexagons, or any other shape.

This patent describes a medical implant comprising a dynamic porous material, wherein the dynamic porous material comprises a porous structure formed of a shape memory material. It is mentioned that the porous structure comprises a regular repeating pattern. The porous structure comprises a honeycomb cellular structure or a dodecahedron cellular structure. The implant comprises a singular structure. The implant has a non-dynamic base and a dynamic surface.

In the present invention the honeycomb structure can be a 3D, such as a dodecahedron structure, similar to buckyball geometry (spherical Fullerene), and can be superelastic and/or have SME (shape memory effect via temperature change). It may also be made up of a repeating pattern of diamonds, hexagons, or any other shape.

In summary, US 201600018410 A1 discloses a surface coating which have a certain 3D honeycome-type porosity. In contrast, the present invention discloses filler particles having a porous surface, but every particle is an individual unity and does not form a continuous coating as disclosed by this patent. In our case, the surface created by the intersection of several particles is discontinuous and non-uniform. Having a superficial porosity that can also cross the thickness of the particle.

Another document is the Chinese patent application CN 10338866145B, which describes a digital modeling method for body preparation design. Where a digital modeling method for tooth body preparation design is described, it belongs to oral digitalization, a medical computer-assisted design field. The method includes four steps: data model building and preprocessing, extraction of teeth, parametric design and modification of the preparation model, and model quality evaluation. The software-based model generation method of this design is simple and has a high degree of automation. It can not only easily generate a dental preparation model that conforms various medical indicators, but it can also allow personalization, parameter modification and quality evaluation of the results. This design method will greatly reduce the time and treatment cost of the dentist's dental preparation, improving the comfort and efficiency of restoration, and has important application value in the field of computer-assisted oral preparation This document describes a digital design method for the preparation of dental models, or is used to calculate the long axis for tooth extraction based on hierarchical geodesic algorithms for extracting long axis teeth.

A third cited document is the European patent WO 2009048314 A1, entitled: A scalable matrix for the in vivo cultivation of bone and cartilage. This invention describes an implant system for the in vivo regeneration of stable bone and cartilage, and in particular to devices specifically shaped as receptacles for scaffold constructs which together form a stable matrix for the regeneration of bone and cartilage in vivo.

The inventors of the present patent application have noted from the literature and personal experience that most bone substitute materials available today, although good at providing osteoconduction (and osteoinduction in some cases), lack the necessary strength to withstand compressive and other forces. Once used, most of these materials do not have the anisotropic properties of bone until healing occurs—a process which takes 6 to 8 weeks. Certain specific shapes, when applied to bone substitute material, metal or plastic (particularly those made using existing SLM or SLS technology) gain compressive strength through stacking. These shapes may be broadly described as polyhedral. They also self-stack, which we herein define as the tendency to form a stable conjoined structure when aggregated together in close proximity in 3-dimensional space. This property is also present in nature and allows seemingly small discrete structures to build into larger robust structures. However, most polyhedral shapes have been described in Euclidean and other geometry but are seldom found in nature. Moreover, it has hitherto been neither obvious nor simple to fabricate such shapes from available materials. The present invention demonstrates the actual fabrication by SLM of polyhedral shapes that are small, stable, can be easily stacked together and possess several other properties more fully described below.

The primary device, which is a unit of the final meso-scale scaffolding system is a polyhedral receptacle. Those well-versed in this area of mathematics and geometry will know that the term polyhedron may be defined as a three-dimensional object composed of a number of polygonal surfaces, which includes but is not limited to all polyhedra described as Platonic, Archimedean, Kepler-Poinsot, having Tetrahedral/Octahedral/Icosahedral symmetry, Non-Convex Snubs, Prisms/Antiprisms, Johnson Solids, Near Misses, Stewart Toroids, Pyramids and generated Cupolae as well as the compound and/or stellated versions of all the aforementioned, including also geodesic spheres, geodesic domes or sections of geodesic spheres and domes.

In particular, of all the known polyhedra, some highly preferred shapes are the dodecahedron, the hexagonal prism, the hexagonal antiprism, the pentagonal dipyramid and the tetrahedron.

This document further describes a receptacle built or formed in the shape of any known polyhedron, with a size upwards of 1 micrometer along any of its dimensions, formed precisely by any method of rapid prototyping (particularly selective laser melting and/or selective laser sintering), or any other fabrication, assembly, extrusion or casting method capable of creating precise three-dimensional shapes using metals, alloys, polymers, ceramic, plastic, gel, or other solid or viscous fluid material, and any combination thereof, for the purpose of implantation directly or indirectly into a cavity, gap, surface or other independent space or zone within the bone or cartilage or other tissue of a mammalian subject where regeneration of bone or cartilage or other tissue is required.

Therefore, in summary, patent WO2009048314 A1 describes a scalable volumetric matrix to completely cover the defect and withstand external biomechanical loads. This matrix can be polyhedral but also in geodesic segments. The present invention discloses particles that, acting individually but interconnected, also cover the defect volumetrically in their entirety, but between the interstices of the particles there is a soft material (usually coagulated blood) that acts as a cushion cushioning the external biomechanical loads. Loads that are also transmitted to particles, which by being able to move freely one from the other distribute the load between them and the soft material in a better way.

The present invention discloses particles that exploit the geometric features of a geodesic segment, but are individual entities that are non-periodically and randomly oriented in the bed to be filled. On the other hand, the previously cited patent discloses of a volumetric matrix (i.e., a continuum) having a periodic and fixed subunit (not particles) organization.

Therefore, the analyzed and submitted documents are not related to the particle of the present application. The present particle can have a large number of features, in particular geodesics, as well as porosity and intrinsic composition (growth factors and chemotaxis factors).

There are documents that explicitly mention the term "geodesic" as a possible geometric structure to be used in a bone filler, but the structure of the regeneration matrix described by said documents is volumetric, continuous and regular.

Bone damage is currently addressed by repairing with bone grafts from the same patient (autografts), which is the alternative with better prognosis but it involves additional surgery in the donor area.

The grafts of ceramic particulate biomaterials are an alternative, but generally have unpredictable results because they consist of solid particles of irregular geometry, which does not favor cell regeneration between particles or much less within them and does not safeguard the vitality of the graft as a whole, especially in larger volume graft center. Multiple studies (Killian et al. 2010, Gentleman et al. 2009, Lunch et al. 2011, Tymchenko et al. 2007, Maduram et al. 2008) suggest that the porosity and geometry of the substrate that makes up the graft promotes cell motility and multiplication and even would have an inductive effect on the differentiation into osteoblasts of adult mesenchymal cells (MSCs) deposited onto these surfaces. Others studies (Mathur et al. 2012; Sanz-Herrera et al. 2009) have shown that cell growth and development is earlier and faster on curved surfaces than on flat surfaces. The question that then arises is how to make small, porous particles having appropriate specific geometries at competitive costs.

An alternative is rapid prototyping (RP) manufacturing technologies, developed by several companies which have been available in the market for years.

Some of the advantages that the present invention provides are:

The present invention relates to a filler particle used as a bone tissue synthetic graft. Said filler particle is elaborated by means 3D printing rapid prototyping technique, thus obtaining a computationally designed filler particle which is then miniaturized and has a complex, non-prismatic, geodesic semi-spherical geometry.

The filler particle obtained through the rapid prototyping technique has a length (between the major longitudinal axis ends) size no greater than 3,000 microns and is made from a material that is a calcium sulfate-rich powder (bioresorbable material), which is subsequently converted into calcium phosphate (biocompatible material) through an ion exchange process carried out in an aqueous medium rich in $PO_4^-$ ions at a given temperature and for a given time.

Particularly, the curvature of the geometry and microporosity of computer design particles are parameterized according to the thickness, length of the geodesic major and minor axes, wherein their curvature radius, apex angle and major and minor axis length will favor cell growth and differentiation into osteoblasts within the bone recipient bed.

The surface is concave on one side and convex on the other (geodesic, semi-spherical);

The microporous surface having interconnected inward canaliculi or tubules allow cellular development and generation of inward vascular networks;

It has a computationally made design, which is studied and calibrated using any CAD software and subsequently miniaturized.

Both the powder and the powder binding liquid in Rapid Prototyping via 3D printing, contain growth and chemotactic factors for mesenchymal stem cells, which are impregnated into the particle and subsequently will be slowly released to the medium, as the particle begins to reabsorb;

When prepared by means of Rapid Prototyping via 3D printing, their production costs decrease significantly.

In summary, we have a bioabsorbable and biocompatible filler particle having geodesic semi-spherical shape (non-obvious geometry), microporous, impregnated with growth factors and MSC-binding proteins, which promotes and facilitates cell multiplication on and within its surface and between the collected particles (osteoconductive, osteoinductive and osteoprogenitor features).

The present invention will additionally allow to introduce into the alloplastic bone fillers market an alternative to favor the recipient bed tissue regeneration taking advantage of the curvature of the surface filling the cavity on which the activity of tissue regeneration is developed, this activity results from the mesenchymal cells that can reach the area or are directly applied as a complementary part to the filling treatment.

The biomaterial particle can also be used in: Traumatology and Orthopedics, Neurosurgery, Maxillofacial Surgery, Oral Surgery.

BRIEF DESCRIPTION OF THE INVENTION

Figure 1:
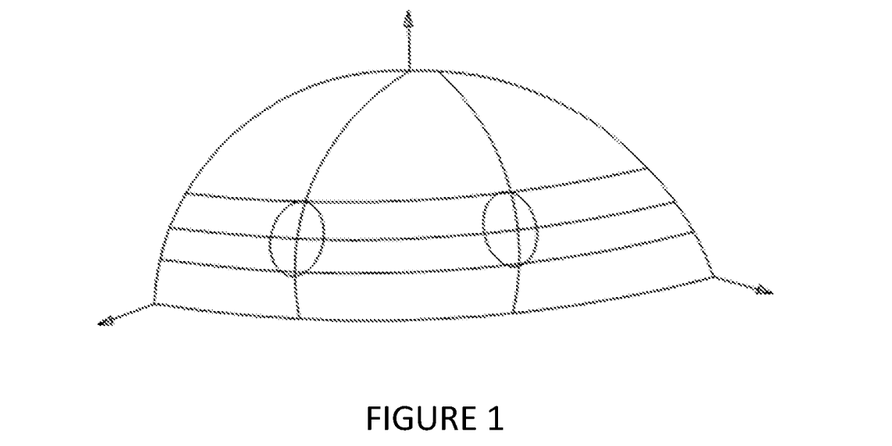
FIG. 1 shows an elevated view of the particle.
Figure 1A:
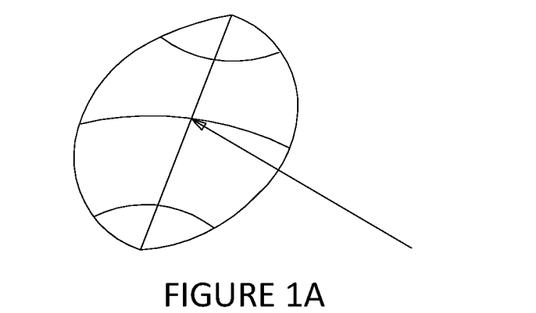
FIG. 1A shows a top perspective view of the particle.
Figure 1B:
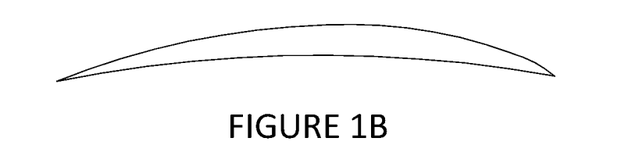
FIG. 1B shows a section of the particle.
Figure 2:
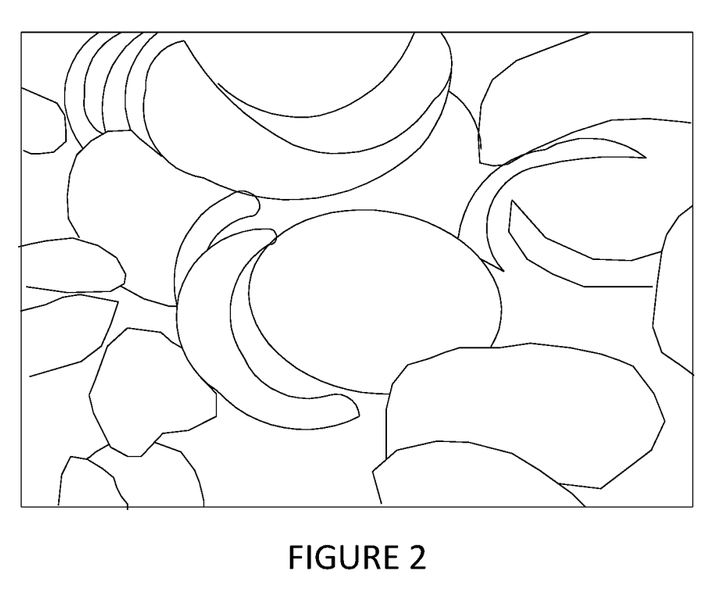
FIG. 2 shows a figure based on a microphotography of a collection of particles.
Figure 3:
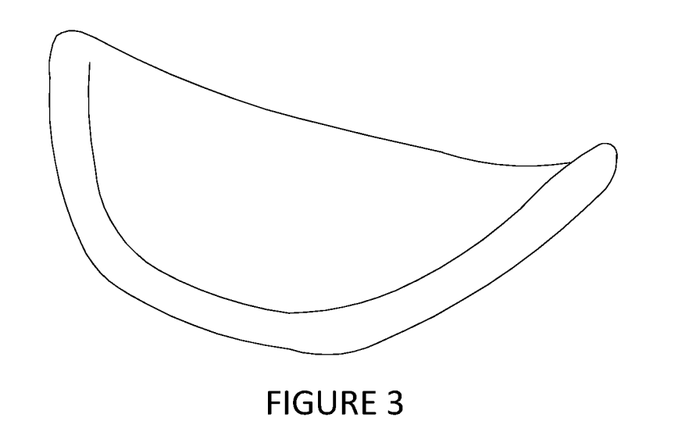
FIG. 3 shows a 3D computational design of a perspective view of a particle.
Figure 4:
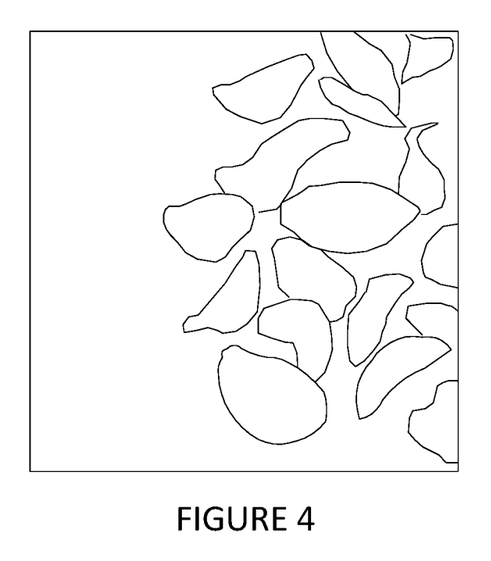
FIG. 4 shows a figure based on a microphotography of fresh particles made by 3D printing rapid prototyping (RP) technique.
Figure 5:
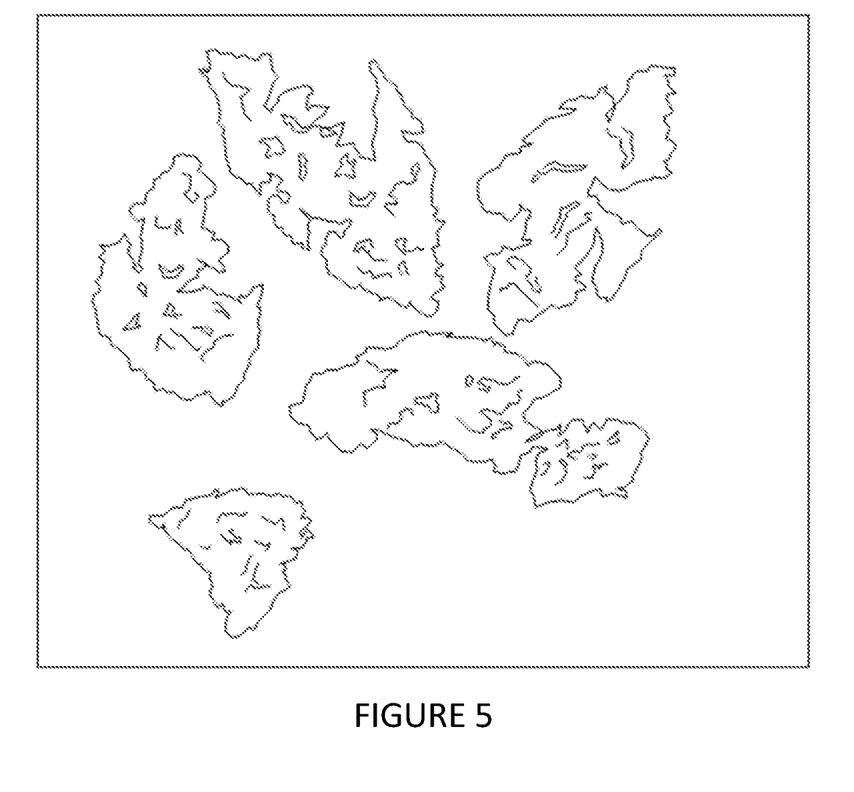
FIG. 5 shows a figure based on a microphotography of grafted particles (Micro-CT image).
Figure 6:
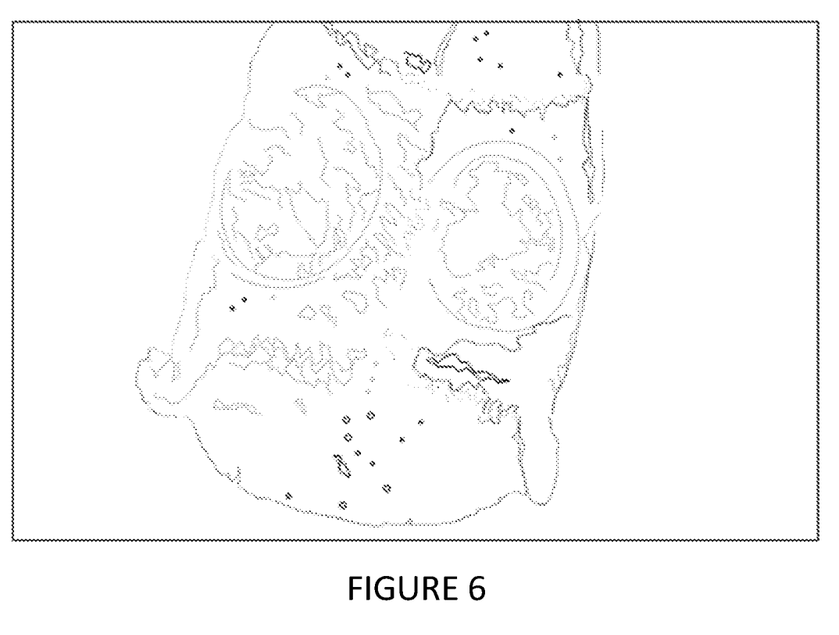
FIG. 6 shows a figure based on a microphotography of bone regeneration in rat cranial vault (Micro-CT image)

The present invention relates to a biologically active microporous filler particle, which works as a bone tissue synthetic graft material made by 3D printing rapid prototyping (RP) technique, this through multiple layers of powder of thin thickness and a liquid injection system, so the liquids jetted on the dust layer are absorbed therein, causing agglomeration of the powder. This results in a particle having a non-prismatic, geodesic semi-spherical, complex geometry. The particle has a size no greater than 3,000 microns and not less than 300 microns long in its largest diameter, and is made from a calcium sulfate-rich powder material (bioresorbable material), the particles are then heated during 15 to 25 minutes at a temperature between 250 and 325° C., said particles are subsequently converted to calcium phosphate (biocompatible material) by an ion exchange process, carried out in an aqueous medium rich in $PO_4^-$ ions at a temperature between 70 and 120° C. for a period of time between 2 and 8 hours. The curvature features of the particles geometry and their microporosity are computationally designed and are parameterized according to the thickness (300-500 microns) and length of the major (500-3,000 microns) and minor (300-1,500 microns) axis of the geodesic segment, its curvature radius, apex angle. The geometry of the filler particle will allow cell growth and differentiation into osteoblasts within the bone recipient bed and between and within the collected particles. It is known that the microtopography of the substrate on which the mesenchymal cells (MSC) are present in the bone bed, affects the magnitude of the contractile forces (hundreds of micro-newtons) that cellular machinery must exert to move or remain attached to the bone surface. In this way, the concave and convex curved surfaces by reducing these contractibility stresses would favor the cellular adhesion, while less concave surfaces would favor the cellular locomotion. On the other hand, the magnitude of the curvature radius (2,000-5,000 microns) of the substrate surface will also influence the differentiation cell lines that mesenchymal cell will have. In this way, the flat and convex surfaces will favor the differentiation into osteoblasts. The concave-convex macrogeometry also safeguards the interconnectivity of particles and their mechanical engagement, a process that occurs when the particles are randomly deposited inside the bone bed or defect, thus favoring compactness and volumetric stability of the whole and at the same time allowing the existence of internal channel network so the tissue can be mobilized and regenerated by the cellular fluid. Additionally, these channels would favor the generation of multiple bone neoformation nuclei inside the graft, not depending only on peripheral neovascularization from the recipient bed. The mechanical strength of calcium sulphate hemihydrate (compressive strength of 2 to 9 Mpa, tensile strength between 1 and 4 Mpa, elastic modulus of 3 to 5.5 Gpa) allow the particles to be handled and applied inside the bed without losing their original shape, but on the contrary and thanks to the coupling favored by their concave-convex surfaces, the graft will result into stable three-dimensional reconstructions, even if any wall of the recipient bed is total or partially absent. Finally, the developed particle can be supplemented with bioactive growth factors or can be applied in conjunction with platelet concentrates or stromal cell concentrates to favor the rate of proliferation and differentiation of mesenchymal cells into osteoblasts within the bone bed to be regenerated, in at least 30%, according to results obtained from in vitro and in vivo preliminary comparative experimental animal tests.

Mechanical strength
Calcium Sulfate Hemidrate

TABLE 1

| Compression strength Mpa | Tensile strength Mpa | Elastic modulus Gpa |
|---|---|---|
| 2-9 | 1-4 | 3-3.5 |

In summary, it is considered appropriate to protect the design and the method of making a bioabsorbable and biocompatible particle, in the form of a microporous, semispherical, geodesic segment impregnated with growth factors, chemotactic factors and MSC binding proteins, which promote and facilitate cell multiplication on its surface; the cell multiplication process, mitosis, which is the division of one cell to produce two others. This is the way in which cells multiply, within and between the collected particles.

DETAILED DESCRIPTION OF THE INVENTION

The present invention relates to a filler particle used as a synthetic graft of bone tissue, dentine tissue.

A filler particle having a complex, non-prismatic, semispherical geodesic geometry is made by 3D printing using a binder jetting method.

The filler particle made by powder bed and binder jetting (mostly water and surfactant) 3D printing technique has a major axis length size no greater than 3,000 microns and is made in a material that is a calcium sulphate rich powder (bioreabsorbable material), which is then converted to calcium phosphate (biocompatible material) by an ion exchange process carried out in an aqueous medium rich in $PO_4^-$ ions (ammonium phosphate solution having a molality of 1-3 M, Table 2) at a temperature between 70 and 120° C. and for 2 to 8 hrs.

TABLE 2

Method of making the biomaterial
Drying of Calcium Sulphate Particles, Ionic
Exchange, Ammonium Phosphate Solution

| Particle | Mole | Ionic Exchange Hours | Temperature ° C. |
|---|---|---|---|
| Calcium sulfate | 1-3 | 2-8 | 70-120 |

In the specific case of the present invention, we have an individual particle with "geodesic" segment geometry, which will form part of the filling. Geodesic geometry is formed by a triangular mesh and, consequently, the triangular structure is self-supported transferring its faces to its vertices called load transfer nodes.

Most commonly this is related to domes or earth geometry due to its shape. "The osculating plane of the geodesic is perpendicular at any point to the plane tangent to the surface. The surface geodesic lines are the "straightest" possible lines (with less curvature) given a point and direction fixed on said surface"

Even though this filler shapes and fills a volumetric space of a bone defect, its stacking does not obey a regular pattern, since it is not a matrix or scaffold or continuous scaffolding but instead it corresponds to a set of deposited particles, which are randomly collected, often with concave-convex coincidences, and which are locked between each other thanks to the irregularity provided by their surface porosity, constituting, as a whole, a stable volumetric scaffolding for bone reconstruction, even without the presence of all the retaining walls of the recipient bed.

In the case of the particle of the present invention the stacking is random. The form in which particles occupy the volume of the bone bed in each case is different, random, often having concave-convex coupling between particles which results in concentric bone neoformation units with interstices between the particles and between these bone formation units.

The location of the interstices is always known or predictable, i.e., especially more rigid, in a regular volumetric pattern, whereas in the case of the present invention this pattern is more flexible and adaptable to the bed type.

The development of this bone filling particulate biomaterial has as main advantages that reparative processes are more predictable and at least 30% faster, recovering the anatomy and function of the damaged structures as soon as possible, allowing the patient to return as soon as possible to normal life.

The object of the present invention is to make a microporous particulate biomaterial having a geodesic segment geometry. The test results indicate that it is possible to print particles in calcium sulphate and then transforming the same into calcium phosphate by ion exchange processes. Initially, the osteoconductive and osteoinductive properties of this particulate biomaterial, manufactured with the RP system, were evaluated by classical in vitro cell development tests, wherein mesenchymal cells, derived from dental pulp, proliferated in intimate contact with and within particles. Subsequently, these mesenchymal cells differentiated into osteoblasts, properties that were evaluated by optical microscopy using calcium deposit staining with Alizarin red and with osteogenic differentiation early markers (expression of RUNX2), taking into account cell morphology. Subsequently, they were evaluated in an in vivo murine experimental model. The images obtained were analyzed with micro-CT, which validated the results of the current scientific literature. It is concluded that the geometry of the particle proposed in the present application favors the attachment of the particles with each other and cell growth between them inside the spaces formed between the topographically curved particle surfaces. This innovation in shape and surface, which allows the attachment of particles, generates concentric units that facilitate cell growth, whereby better results are obtained in large volume grafts, with neovascularization focus in the center of the graft and not just on the walls of the recipient bed. This bone filler particle would be directed to satisfying the surgical needs of orthopedists, neurosurgeons, maxillofacials and general dentists, faced with the challenge of filling defects or bone cavities of a certain volume (greater than a cubic centimeter), with a good prognosis, especially if these have great volume. The present invention also represents an interesting economy in both national and global health area, by enabling the production of large quantities of printed particles by rapid prototyping with a very low production cost.

The biomaterial of the present invention may be applied in:

Bone graft in osteotomies and vertebral column arthrodesis (Traumatology and Neurosurgery)

Bone graft as filler in hip prosthesis insertion (Traumatology)

Bone graft for sealing of craniotomies (Neurosurgery)—

Bone graft of residual cavities in jaw or maxilla, after eliminating cystic or tumoral lesion (Oral/Maxillofacial Surgery)—

Bone graft in the recovery of residual alveolar bone ridge height (Oral Surgery)

Graft of residual alveoli after an exodontia (Oral Surgery)

The elements that are used to make the particulate biomaterial of the present invention are:
i. Calcium sulfate, powder.
ii. 3D Printing via Rapid Prototyping
iii. Stem cells derived from dental pulp Method of Making the Biomaterial:

The calcium sulphate particles are dried, then subjected to ion exchange in ammonium phosphate solution for 2 to 8 hours and at a temperature between 70 and 120° C., then the resulting particles are washed in distilled water for 2 to 5 minutes, then dried on absorbent paper in contact with atmospheric air for 1 hour.

Particles were generated according to the previously described technique.

i) The generated particles were deposited on culture plates with mesenchymal stem cells from various sources (fatty tissue, dental pulp, dental papilla) resulting in cell development on their surface in all the alternatives;

ii) The particles were used as a scaffold for all the studied stem cell sources;

iii) The particles were left for 12 hours in a culture medium (D-MEM) with stem cells, which resulted in adhesion and incorporation of the cellular elements on their surface and inwards.

iv) The particles "loaded" with stem cells were grafted onto bone defects experimentally created in the cranial vault of a rat, obtaining results that demonstrate a bone neoformation at least 30% faster and more effective than on the control side.

Application Example

Method of making the biomaterial:

The calcium sulphate particles are dried in an oven at 300° C. for 10 minutes, then subjected to ion exchange in ammonium phosphate solution for 4 hours at a temperature of 80° C., then the resulting particles are washed in distilled water for 3 minutes, then dried on absorbent paper in contact with atmospheric air for 1 hour.

Particles were generated according to the previously described technique.

i) The generated particles were deposited on culture plates with mesenchymal stem cells of dental pulp, resulting in cell development.

ii) The particles were used as a scaffold for the studied stem cell source;

iii) The particles were left for 12 hours in a culture medium (D-MEM) with stem cells, which resulted in adhesion and incorporation of the cellular elements on their surface and inwards.

iv) The particles "loaded" with stem cells were grafted onto bone defects experimentally created in the cranial vault of a rat, obtaining results that demonstrate a bone neoformation at least 30% faster and more effective than on the control side.

Experiment: Experimental model carried out in a rat cranial vault (skull).

The rat surgical protocol was the following, differing only in the bioparticle used in left parietal and right parietal, bioparticles with physiological saline were used in the latter.

Trepanation 1: cranial vault, left parietal

Bioparticles with DP-MSC (mesenchymal cells derived from dental pulp)

Trepanation 2: cranial vault, right parietal ⟶ Bioparticles with PS (physiological saline)

Details of the protocol are:

Specimen in dorsal decubitus, secure to operative table with ad hoc cephalic support.

Operative field, with povidone iodine.

Cranial approach with antero-posterior oblique linear incision of the dermal and periosteal plane.

Exposure of the bone plane of the cranial vault, at both sides of the midline.

Trepanation of the left parietal bone, with trephine of 5.0 mm external diameter, with preservation of the dura mater.

Trepanation is repeated on the right side of the midline, separated by a 3 mm bone bridge from the left paramedian trepanation.

Surgical cleaning of both surgical beds, hemostasis and grafting of:

GeoBone® particles impregnated with DP-MSC in the left trepanation

GeoBone® particles impregnated with physiological saline in the right side;

Both trepanations are covered with a guided regeneration resorbable membrane sheet (for clinical use, available on the market).

Close on a plane, with Ethilon 3-0.

Results

TABLE 3

Test Rat 1: analysis at 15 days: Left hole

| Thickness distribution range in μm | Thickness distribution mean range in μm | Volume in μm³ | Volume range in % |
|---|---|---|---|
| 17.42-<52.26 | 34.84 | 829243057 | 8.9634 |
| 52.26-<87.11 | 69.69 | 1475346668 | 15.9471 |
| 87.11-<121.95 | 104.53 | 1319098906 | 14.2582 |
| 121.95-<156.79 | 139.37 | 1588988614 | 17.1755 |
| 156.79-<191.63 | 174.21 | 1215497719 | 13.1384 |
| 191.63-<226.48 | 209.06 | 848457444 | 9.171 |
| 226.48-<261.32 | 243.9 | 820080004 | 8.8643 |
| 261.32-<296.16 | 278.74 | 398685325 | 4.3094 |
| 296.16-<331.00 | 313.58 | 291858828 | 3.1547 |
| 331.00-<365.85 | 348.43 | 170370390 | 1.8415 |
| 365.85-<400.69 | 383.27 | 58076729.1 | 0.6278 |
| 400.69-<435.53 | 418.11 | 41654085.2 | 0.4502 |
| 435.53-<470.38 | 452.95 | 120838089 | 1.3061 |
| 470.38-<505.22 | 487.8 | 73283272 | 0.7921 |

Conclusion: This sample shows the presence of segmented structures of larger size compared to the right side of the same rat.

TABLE 4

Test Rat 1: analysis at 15 days: Right hole

| Thickness distribution range in μm | Thickness distribution mean range in μm | Volume in μm³ | Volume range in % |
|---|---|---|---|
| 17.42-<52.26 | 34.84 | 1287903285 | 17.2697 |
| 52.26-<87.11 | 69.69 | 1929851005 | 25.8777 |
| 87.11-<121.95 | 104.53 | 1312738171 | 17.6027 |
| 121.95-<156.79 | 139.37 | 1262243564 | 16.9256 |
| 156.79-<191.63 | 174.21 | 862109494 | 11.5602 |
| 191.63-<226.48 | 209.06 | 482146829 | 6.4652 |
| 226.48-<261.32 | 243.9 | 258865494 | 3.4712 |
| 261.32-<296.16 | 278.74 | 61725030.6 | 0.8277 |

Conclusion: There is less presence of large objects and the object size range is around 70 μm. In addition, the large object total volume is much smaller than in the cavity of the left hole.

Results

TABLE 6

Test Rat 2: analysis at 45 days: Left hole.

| Thickness distribution range in μm | Thickness distribution mean range in μm | Volume in μm³ | Volume range in % |
|---|---|---|---|
| 17.42-<52.26 | 34.84 | 478625425 | 30.9512 |
| 52.26-<87.11 | 69.69 | 402349488 | 26.0187 |
| 87.11-<121.95 | 104.53 | 186861770 | 12.0838 |
| 121.95-<156.79 | 139.37 | 100946915 | 6.5279 |
| 156.79-<191.63 | 174.21 | 95146644.3 | 6.1528 |
| 191.63-<226.48 | 209.06 | 78872047.4 | 5.1004 |
| 226.48-<261.32 | 243.9 | 135960034 | 8.7921 |
| 261.32-<296.16 | 278.74 | 67625761.6 | 4.3731 |

Conclusion: The same tendency as seen in the previous rat can be observed in the left cavity of this rat, but with a smaller size distribution and with a tendency to have larger sizes than the right one.

TABLE 7

Test Rat 2: analysis at 45 days: right hole.

| Thickness distribution range in μm | Thickness distribution mean range in μm | Volume in μm³ | Volume range in % |
|---|---|---|---|
| 17.42-<52.26 | 34.84 | 309925852 | 45.2246 |
| 52.26-<87.11 | 69.69 | 203004182 | 29.6225 |
| 87.11-<121.95 | 104.53 | 82414600.9 | 12.026 |
| 121.95-<156.79 | 139.37 | 45984460.4 | 6.7101 |
| 156.79-<191.63 | 174.21 | 33442763.3 | 4.88 |
| 191.63-<226.48 | 209.06 | 10532487.7 | 1.5369 |

Conclusion: The same tendency seen in the previous rat can be observed in the right cavity of this rat, but with a smaller size distribution and with a tendency to have smaller sizes than the left cavity.

The invention claimed is:

1. A particulate biomaterial, comprising calcium salt particles having non-prismatic, semi-spherical, geodesic shapes used as a filler or substitute medium for bone tissue, wherein the calcium salt particles are selected from the group consisting of tricalcium phosphate, calcium phosphate, calcium sulfate, and calcium sulfate hemihydrate.

2. The particulate biomaterial according to claim 1, wherein said particles have non-prismatic, semi-spherical, geodesic forms elaborated by using 3D printing rapid prototyping (RP).

3. The particulate biomaterial according to claim 2, wherein the particle geometry is computationally designed, parameterized according to a thickness of the geodesic, a radius of curvature, an apex angle and major axis length.

4. The particulate biomaterial according to claim 3, wherein the particle geometry allows the growth and cell differentiation of mesenchymal cells (MSC) into osteoblasts within the bone recipient bed.

5. The biomaterial according to claim 1, wherein the particle is a bioabsorbable and biocompatible, microporous, semi-spherical geodesic particle impregnated with growth factors and MSC binding protein, which facilitates cell multiplication on its surface, within its surface and between the collected particles.

6. The biomaterial according to claim 1, wherein the random stacking in the form on which particles occupy the volume of a bone bed is modified in each particular case, but the interstices between the particles remain geodesic.

7. The biomaterial according to claim 1, wherein the volumetric pattern regulating the interstices location, is flexible and adaptable to the bed type.

8. A method of making a particulate biomaterial according to claim 1, comprising the steps of:
   i) adding water and surfactant as binder to the particles previously printed with powder rapid prototyping (RP) technique system;
   ii) subjecting the powder in an ammonium phosphate solution with molality of 1-3 mol to ion exchange at temperatures between 70-120° C. during 2-8 hours to obtain calcium phosphate;
   iii) obtaining the powder formed by bioparticles and forming the particulate filling biomaterial.

9. The method of making a particulate biomaterial according to claim 8, wherein 3D printing powder for rapid prototyping contains growth and chemotactic factors for mesenchymal stem cells that are impregnated in the particle.

10. The method of making the bioparticles of claim 1 for use as bone filler, wherein the particles are made according to the following method:
   i) generating particles and depositing on culture plates with mesenchymal stem cells from diverse sources and obtaining a cellular development on their surface in all the alternatives;
   ii) the particles are useful as scaffolds for all the studied stem cell sources;
   iii) leaving the particles for 12 hours in a culture medium with stem cells, which result in adhesion and incorporation of the cellular elements on their surface and inwards;
   iv) grafting the particles "loaded" with stem cells onto bone defects in the bone tissue.

11. The biomaterial according to claim 1, wherein the biomaterial particle can be used in traumatology and orthopedics, neurosurgery, maxillofacial surgery, oral surgery.

12. The biomaterial according to claim 1, wherein the biomaterial particles can be used in:
   Bone graft in osteotomies and vertebral column arthrodesis;
   Bone graft as filler in hip prosthesis insertion;
   Bone graft for sealing of craniotomies;

Bone graft of residual cavities in jaw or maxilla, after eliminating cystic or tumoral lesion;
Bone graft in the recovery of residual alveolar bone ridge height;
Graft of residual alveoli after an exodontia.

* * * * *